| United States Patent [19] | [11] 4,031,229 |
| --- | --- |
| Konig et al. | [45] June 21, 1977 |

[54] PENICILLINS AND PROCESSES FOR THEIR PREPARATION AND USE

[75] Inventors: Hans-Bodo König; Karl Georg Metzger; Wilfried Schröck, all of Wuppertal, Germany

[73] Assignee: Bayer Aktiengesellschaft, Leverkusen, Germany

[22] Filed: June 4, 1976

[21] Appl. No.: 692,930

[30] Foreign Application Priority Data

June 24, 1975  Germany .......................... 2528079

[52] U.S. Cl. .............................. 424/271; 260/239.1
[51] Int. Cl.² .............. A61K 31/43; C07D 499/66; C07D 499/68; C07D 499/70
[58] Field of Search .................. 260/239.1; 424/271

[56] References Cited

UNITED STATES PATENTS

| 3,959,258 | 6/1976 | König et al. ..................... 260/239.1 |
| 3,966,709 | 6/1976 | König et al. ..................... 260/239.1 |
| 3,972,870 | 8/1976 | König et al. ..................... 260/239.1 |
| 3,975,375 | 8/1976 | König et al. ..................... 260/239.1 |

*Primary Examiner*—Gerald A. Schwartz
*Attorney, Agent, or Firm*—Burgess, Dinklage & Sprung

[57] ABSTRACT

6-[α-(Imidazolidin-2-on-1-carbonylamido)acetamido]-penicillanic acids substituted in the 3-position of the imidazolidinone ring with phenyl or a substituted phenyl group and on the α-carbon atom of the acetamido bridge with a phenyl, thienyl, cyclohexenyl or cyclohexadienyl group, and their salts, are antibacterial agents. The compounds, of which α-(3-phenylimidazolidin-2-on-1-ylcarbonylamino)benzylpenicillin is a representative example, are prepared by acylation of the corresponding 6-(α-aminoacetamido)penicillanic acid or a derivative thereof.

15 Claims, No Drawings

PENICILLINS AND PROCESSES FOR THEIR PREPARATION AND USE

The present invention relates to new β-lactams, to a process for their preparation and their use as medicaments, especially as antibacterial agents and growth promoting agents.

It is known that certain α-(imidazolidin-2-oxo-1-ylcarbonylamino)phenacetyl derivatives of 6-aminopenicillanic acid and 7-aminocephalosporanic acid have an anti-bacterial activity; see e.g. German O.S. 2,104,580, 2,152,967, 2,258,973, 2,402,465 and 2,428,139.

The present invention pertains to β-lactams of the formula:

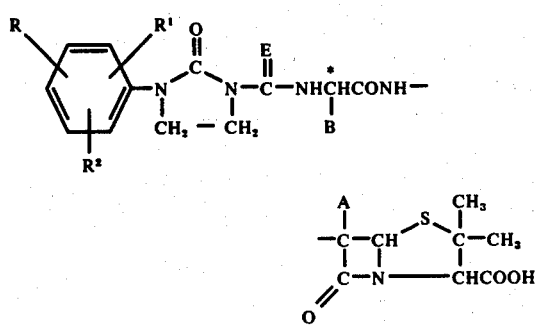

and the pharmaceutically acceptable salts thereof, wherein
the carbon atom designated * constitutes a center of chirality;
A is hydrogen or methoxy;
B is phenyl, hydroxyphenyl, halophenyl, methoxyphenyl, cyanophenyl, methylsulfonylphenyl, thienyl, cyclohexenyl or cyclohexa-1,4-dien-1-yl;
each of R, $R^1$ and $R^2$ is independently selected from the group consisting of hydrogen, halo, lower alkyl, halo(lower)alkyl, carboxy, formyl, carbo(lower alkoxy), lower alkanoyl, cyano, carbamyl, lower alkylcarbamyl, di(lower alkyl)carbamyl, amino, lower alkylamino, di (lower alkyl)amino, pyrrolidino, piperidino, formamido, lower alkanamido, N-(lower alkyl)formamido, N-(lower alkyl)lower alkanamido, lower alkylidenimino, lower alkylsulfonamido, N-(lower alkyl)lower alkylsulfonamido, sulfamino, N-(lower alkyl)sulfamino, amidino, di(lower alkyl)aminomethylidenimino, pyrrolidinomethylidenimino, guanido, nitro, azido, carbo(lower alkoxy)amino, N-(lower alkyl)carbo(lower alkoxy)-amino, hydroxy, lower alkoxy, formyloxy, lower alkanoyloxy, lower alkoxycarbonyloxy, carbamyloxy, N-(lower alkyl)carbamyloxy, N,N-di(lower alkyl)-carbamyloxy, pyrrolidinocarboxyloxy, sulfamyloxy, N-(lower alkyl)sulfamyloxy, N,N-di(lower alkyl)-sulfamyloxy, mercapto, lower alkylthio, trifluoromethylthio, lower alkylsulfonyl, sulfo, lower alkylsulfinyl, trifluoromethylsulfonyl, sulfamyl, N-(lower alkyl)sulfamyl, N,N-(lower alkyl)sulfamyl, pyrrolidinosulfonyl, and sulfothio; and
E is oxygen or sulfur.

The foregoing compounds possess several centers of chirality [see Cahn et al., Angew. Chem. Internat. Edit., 5, (1966) No. 4, 385 et seq.]. With respect to those in the β-lactam nuclei itself, the configuration about each chirality center corresponds to that of the naturally occurring molecule. With respect to other centers of chirality, and in particular to the carbon atom designated C*, the configuration can be either in form; i. e., the R form or the S form. All of the individual diastereomers and isomers, as well as mixtures thereof, are within the scope of the present invention.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkylidene denotes a geminally bivalent but otherwise saturated branched or straight hydrocarbon chain containing from 1 to 6 carbon atoms. Representative of such alkyl groups are thus methylidene, ethylidene, propylidene, isopropylidene, butylidene, isobutylidene, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term lower alkylthio denotes a branched or straight hydrocarbon chain of 1 to 6 carbon atoms bound to the remainder of the molecule through a divalent sulfur as, for example, methylthio, ethylthio, propylthio, isopropylthio, butylthio, and the like.

The term halo denotes the monovalent substituents fluoro, chloro, bromo and iodo.

When B is phenyl, it can be unsubstituted or substituted by one to three identical or different substituents, preferably one or two and especially one, of the above mentioned substituents. In the case of monosubstitution, the substituent is preferably in the 4-position. Particularly preferred substituents are chloro, hydroxy or methoxy. Preferentially, B is phenyl, 4-hydroxyphenyl and 1,4-cyclohexadien-1-yl.

The methoxy group designated by A represents known molecular variations in penicillin chemistry. Preferably A is hydrogen.

R, $R^1$ and $R^2$ can be alike or different and include hydrogen, halo, preferably fluoro, chloro or bromo; lower alkyl, preferably methyl, ethyl, propyl or isopropyl and especially methyl and ethyl; halo lower alkyl which is substituted with one to three identical or different halo atoms preferably fluoro, chloro or bromo and especially fluoro and chloro, such as trifluoromethyl, chlorodifluoromethyl and 2,2,2-trifluoroethyl; lower alkanoyl (—CO-lower alkyl) such as acetyl, propionyl or α-methylpropionyl, especially acetyl; carbo lower alkoxy (—COO—lower alkyl) such as carbomethoxy, carbethoxy, carbisopropoxy, and carbo-t.-butoxy, especially carbomethoxy and carbethoxy; carbamyl; lower alkyl carbamyl such as methylcarbamyl, ethylcarbamyl and isopropylcarbamyl; di(lower alkyl)-carbamyl such as dimethylcarbamyl and diethylcarbamyl; lower alkylamino such as methylamino or ethylamino; di(lower alkyl)amino such as dimethylamino or diethylamino; lower alkanamido such as acetamido; N-(lower alkyl)formamido such as N-methylformamido and N-ethylformamido; N-(lower alkyl)-lower alkanamido such as N-methylacetamido; lower alkylidenimino such as isopropylidenimino; lower alkylsulfonamido such as $CH_3SO_2NH$ or $C_2H_5SO_2NH$—; N-(lower alkyl)lower alkylsulfonamido such as $CH_3SO_2N(CH_3)$—; N-(lower alkyl)sulfamido such as $HO_3SN(C_2H_5)-$, di(lower alkyl)-aminomethylidenimino such as $(CH_3)_2N-CH=N-$, carbo(lower alkoxy)-amino such as $CH_3OCONH-$ or $C_2H_5OCONH-$; N-lower alkyl-carbo-(lower alkyl)amino such as $CH_3OCON(CH_3)-$; lower alkoxy, preferably methoxy or ethoxy; lower alkanoyloxy, preferably acetoxy, propionyloxy and α-methylpropionyloxy; lower alkoxy-carbonyloxy such as $CH_3OCOO-$, $C_2H_5OCOO-$ or $(CH_3)_3COCOO-$; carbamyloxy; lower alkylcarbamyloxy such as $CH_3NHCOO$ or $C_2H_5NHCOO-$, di(lower alkyl)carbamyloxy such as $(CH_3)_2NCOO-$ or $(C_2H_5)_2NCOO-$; N-(lower alkyl)-sulfamyloxy such as $CH_3NHSO_3-$ or $C_2H_5NHSO_3-$; di(lower alkyl)sulfamyloxy such as $(CH_3)_2NSO_3-$ or $(C_2H_5)_2NSO_3-$; lower alkylthio, preferably methylthio, ethylthio, isopropylthio; trifluoromethylthio; lower alkylsulfinyl, methylsulfinyl or ethylsulfinyl; lower alkylsulfonyl, preferably methylsulfonyl, ethylsulfonyl; trifluoromethylsulfonyl; sulfamyl; lower alkylsulfamyl such as $CH_3NHSO_2-$ or $C_2H_5NHSO_2-$ and di(lower alkyl)sulfamyl such as $(CH_3)_2NSO_2-$ or $(C_2H_5)_2NSO_2-$.

Pharmaceutically acceptable salts of these compounds, as well as of the starting compounds, are salts of these compounds with organic or inorganic bases at the depicted carboxylic acid and sulfonic acid groups. Bases which can be employed for this purpose are all the bases customarily used in pharmaceutical chemistry, especially in the chemistry of antibiotics. Examples of inorganic bases which may be mentioned are; alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate, sodium bicarbonate and potassium bicarbonate; aluminium hydroxide and ammonium hydroxide. Organic bases which can be employed are primary, secondary and tertiary aliphatic amines as well as heterocyclic amines. Examples which may be mentioned are: di- and tri-lower alkylamines, for example diethylamine and triethylamine, tri-β-hydroxytriethylamine, tri-β-hydroxyethylamine, procaine, dibenzylamine, N,N'-dibenzylethylenediamine, N-benzyl-β-phenyl-ethylamine, N-methylmorpholine and N-ethyl-morpholine, 1-ephenamine, dehydroabietylamine, N,N'-bis-dihydroabietylethylenediamine and N-lower alkylpiperidine. So-called basic amino-acids, such as lysine and arginine, can also be used advantageously as bases. Particularly preferred salts are the sodium salts.

In a first preferred embodiment, the invention pertains to a β-lactam of the formula:

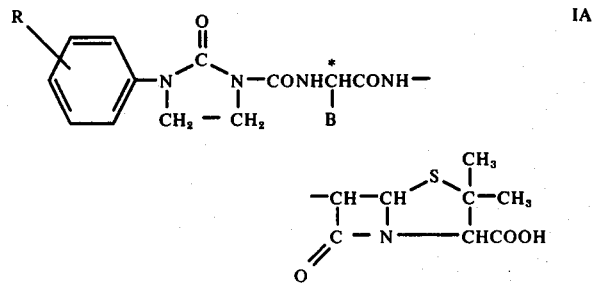

and the pharmaceutically acceptable salts thereof, wherein the carbon atom designated * constitutes a center of chirality;

B is phenyl, hydroxyphenyl, chlorophenyl, cyclohexenyl or cyclohexa-1,4-dien-1-yl; and R is hydrogen, halo, cyano, lower alkoxy or lower alkylsulfamyl.

Among the foregoing compounds, those which are particularly preferred are those wherein B is phenyl, 4-hydroxyphenyl or cyclohexa-1,4-dien-1-yl; and R is hydrogen, chloro, cyano, methoxy or methylsulfamyl.

The sodium salts and the compounds of the D-configuration about the carbon atom designated * are also preferred.

The compounds are prepared according to a process which comprises allowing a β-lactam of the formula:

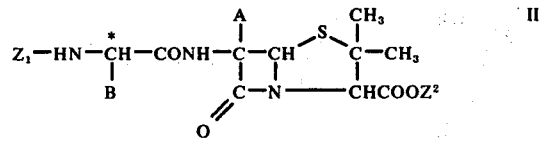

wherein A and B are as defined above, and each of $Z^1$ and $Z^2$ is independently hydrogen or a silyl group, to react with an imidazolidin-2-on-1-carboxylic acid derivative of the formula:

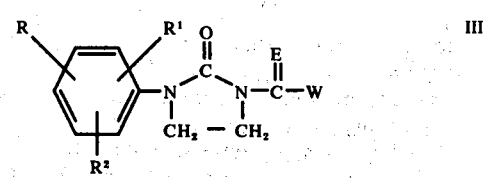

wherein

R, $R^1$ and $R^2$ are as defined above and

W is halo, azido, phenoxy, 4-nitrophenoxy, 2,4,5-trichlorophenoxy, benzylthio, isopropylideniminooxy, succimidooxy, phthalimidooxy or benztriazol-1-yloxy, at a temperature of from about −20° C to about +50° C in the presence of a solvent and, if desired, in the presence of a base, and when one or both of $Z^1$ and $Z^2$ are a silyl group.

A mono or disilyl derivative can be used. Preferably either both $Z^1$ and $Z^2$ are hydrogen or $Z^2$ is silyl with $Z^1$ being silyl or hydrogen. Typical silyl groups include tri(lower alkyl)silyl and mono(lower alkyl-di-(lower alkoxy)silyl such as trimethylsilyl, dimethylisopropylsilyl and methyl-dimethoxysilyl.

The compounds of Formula II are known or are readily obtainable according to known methods; see, e.g. Flynn, Cephalosporins and Penicillins, Academic Press, New York and London, (1972). All crystal forms, hydrate forms, solvate forms, molecule complexes and salts of the compounds of Formula II are suitable as starting materials. Examples include α-aminobenzylpenicillin (ampicillin), α-amino-4-methylbenzylpenicillin, α-amino-p-chlorobenzylpenicillin, α-amino-4-hydroxy-benzylpenicillin (amoxicillin) and 6-[2-amino-2-(1,4-cyclohexadien-1-yl)-acetamido]-penicillanic acid (epicillin) as well as their mono- and ditrimethylsilyl derivatives. The conversion of compounds of Formula II in which $Z^1$ and $Z^2$ are hydrogen to the corresponding silyl derivatives is carried out in a known manner using the customary silylating agents, such as, for example, trimethylchlorosilane or dimethyl-t-butyl-chlorosilane.

The compounds of Formula III are also known or are easily obtainable according to known methods. They can, for example, be prepared by allowing molar amounts of a phenylimidazolidinone of the formula:

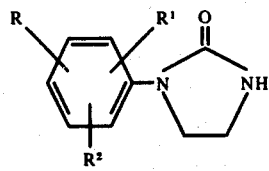

IV in which R, R¹ and R² are as defined above,
to react with a compound of the formula:

$$W\underset{\underset{E}{\|}}{C}W$$

in which W is as defined above,
as for example phosgene or thiophosgene, in an inert organic solvent such as tetrahydrofuran, or in mixtures of water and inert organic solvents such as chloroform, optionally in the presence or absence of for example a molar amount of a base such as triethylamine, at temperatures of from about −5° to about 25° C.

When W is not halogen, the compounds of Formula III can be easily prepared from compounds of Formula III in which W is halogen, by reaction with compounds of the formula H-W, in which W is as defined above other than halogen, in the prsence of a base such as triethylamine, in inert organic solvents such as tetrahydrofuran, or mixtures of water and inert organic solvents such as chloroform.

Examples of compound of Formula III which may be mentioned are:

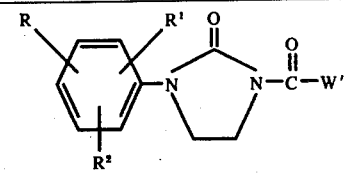

| R | R¹ | R² | W' |
|---|----|----|-----|
| H | H | H | Cl |
| 2-Cl | H | H | Cl |
| 3-Cl | H | H | N₃ |
| 4-Cl | H | H | Cl |
| 2-Cl | 4-Cl | H | Cl |
| 2-CH₃ | H | H | Cl |
| 3-CH₃ | H | H | Cl |
| 4-CH₃ | H | H | Cl |
| 2-CH₃ | 3-CH₃ | H | Cl |
| 2-C₂H₅ | H | H | Cl |
| 3-C₂H₅ | H | H | Cl |
| 2-CH₃O | H | H | Cl |
| 3-CH₃O | H | H | Cl |
| 4-CH₃O | H | H | Cl |
| 2-C₂H₅O | H | H | Cl |
| 4-C₂H₅O | H | H | Cl |
| 4-C₂H₅O | 2-CH₃ | H | Cl |
| 2-CN | H | H | Cl |
| 3-CN | H | H | Cl |
| 4-CN | H | H | Cl |
| 4-CH₃NHSO₂ | H | H | Cl |
| 4-HOSO₂ | H | H | Cl |
| 2-Br | 3-Cl | H | Cl |
| 2-Br | 4-Cl | H | Cl |
| 3-CF₃ | H | H | Cl |
| 2-OH | H | H | Cl |
| 3-OH | H | H | Cl |
| 4-OH | H | H | Cl |

-continued

| R | R¹ | R² | W' |
|---|----|----|-----|
| 4-COOH | H | H | Cl |

If D-α-aminobenzylpenicillin and 1-chlorocarbonyl-3-phenylimidazolidin-2-one are utilized as starting materials, the course of the reaction can be diagrammatically depicted as follows:

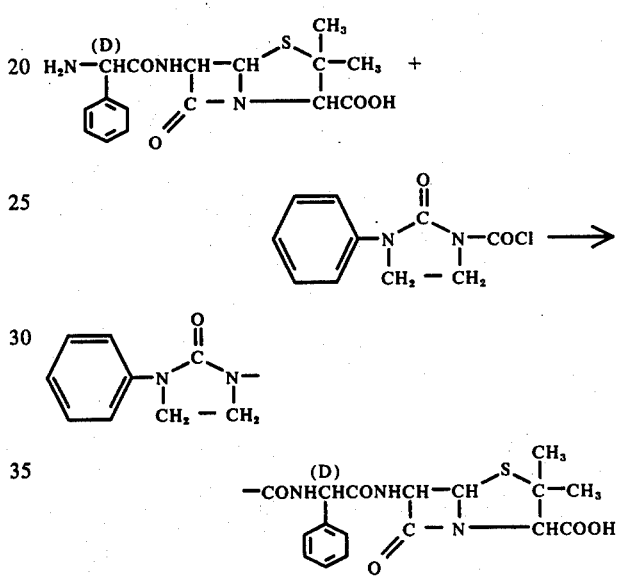

Diluents or solvents which can be used in the process include all the customary inert organic solvents as well as water and mixtures of water and organic solvents. If compounds of Formula II in which Z¹ and Z² represent hydrogen, or Z¹ represents hydrogen and Z² represents a silyl group which is relatively stable to solvolysis, or Z¹ and Z² represent silyl groups which are relatively stable to solvolysis such as for example silyl groups of the types Si(CH₃) (OCH₃)₂ and Si(CH₃)₂ (OCH₃), are used as starting materials, the reaction can be carried out in any desired mixture of water with water-miscible organic solvents. These include ketones such as acetone, cyclic ethers such as tetrahydrofuran or dioxane, nitriles such as acetonitrile, formamides such as dimethylformamide, dimethylsulfoxide, or alcohols such as isopropanol. During the reactions, the pH of the reaction mixture is maintained in a range of about 1.5 to 9.5, for example between pH 6.5 and 8.0, by use of a buffer or the addition of base. The reaction according to the invention can, however, also be carried out in another pH range, for example between 4.5 and 9.0 or at pH 2.0 to 4.5. Furthermore, it is possible to carry out the reaction in solvents which are immiscible with water, for example halogenated hydrocarbons such as chloroform or methylene chloride, with the addition of bases, preferably triethylamine, diethylamine or N-ethylpiperidine. In addition, the reaction can be carried out in a mixture of water and a solvent which is immiscible with water, for example ethers such as diethyl ether, halogenated hydrocarbons such as chloroform or methylene chloride, carbon disulfide, ketones such as isobutyl methyl ketone, esters such as ethyl acetate, or aromatic solvents such as benzene. In this case, it is appropriate to maintain vigorous stirring and to maintain the pH value in a range of from about 1.5 to about 9.5, for example between 4.5 and 9.0 or between 2.0 and 3.0. by addition of base or by use of a buffer. The reaction can also be carried out in water alone in the absence of organic solvents, in the presence of an organic or inorganic base or with the addition of buffer substances. If compounds of Formula II in which $Z^1$ is hydrogen and $Z^2$ is a silyl group having little resistance to solvolysis, or $Z^1$ and $Z^2$ are both silyl groups which have little resistance to solvolysis, as for example of the type $Si(CH_3)_3$, the reaction is preferably carried out in non-aqueous solvents which are free of hydroxyl groups. These include halogenated hydrocarbons as for example methylene chloride or chloroform, benzene, tetrahydrofuran, acetone or dimethylformamide and the like. In this case, the addition of bases is generally not necessary, although it can be advantageous in some isolated cases, but not all, in order to improve the yield and purity of the products. The bases, which can be added are either tertiary aliphatic or aromatic amines such as pyridine or tertiary alkylamines for example triethylamine, or secondary amines which are difficult to acylate because of stearic hindrance, such as dicyclohexylamine. The amount of the bases used depends on the pH value sought. When measurement and adjustment of the pH is not carried out, or when this is not possible or not meaningful because of the lack of adequate amounts of water in the diluent, 1 to 2.5, in particular 1.5 to 2.0, molar equivalents of base are generally employed with compounds of Formula II in which $Z^1$ and $Z^2$ are hydrogen. When compounds of Formula II in which $Z^1$ is hydrogen and $Z^2$ is a silyl group, or in which $Z^1$ and $Z^2$ are both silyl groups, are used, either no base is used or, preferably, 0.5 to 2, especially 1, molar equivalents of base are used. Bases which can be used include all the organic and inorganic bases customarily used in organic chemistry, such as alkali metal hydroxides and alkaline earth metal hydroxides, alkaline earth metal oxides, alkali metal carbonates and bicarbonates and alkaline earth metal carbonates and bicarbonates, ammonia, primary, secondary and tertiary aliphatic and aromatic amines and heterocyclic bases. Examples which may be mentioned are sodium hydroxide, potassium hydroxide and calcium hydroxide, calcium oxide, sodium carbonate and potassium carbonate, sodium bicarbonate and potassium bicarbonate, ethylamine, methylethylamine, triethylamine, hydroxyethylamine, aniline, pyridine and piperidine. When the silylated starting materials are used, the above mentioned restrictions with regard to the nature of the bases should be observed. Buffering systems include all the customary buffers such as for example phosphate buffers, citrate buffers and tris-(hydroxymethyl)aminomethane buffer.

The reaction temperatures can be varied within a relatively wide range but in general is from about $-20°$ to about $+50°$ C, preferably between $0°$ and $+20°$ C. Although the reaction can be carried out under elevated pressure, generally normal pressure is employed.

The reactants can be used in equimolar amounts. However, it is often desirable to use one of the two reactants in excess in order to facilitate the purification, or the preparation in a pure state, of the desired penicillin and to increase the yield. For example, it is possible to employ the reactants of Formula II in an excess of about 0.1 to about 1, preferably from 0.1 to 0.3, molar equivalents, based on the starting compound of Formula III. This results in less decomposition of the reactants of Formula III in an aqueous solvent mixture. The excess can be easily removed in working up the reaction mixture by utilizing its good solubility in aqueous mineral acids.

On the other hand, it is also possible to advantageously employ the reactants of Formula III in excess for example, about 0.1 to about 1.5, preferably from 0.1 to 1.0, molar equivalents. This results in better utilization of the reactants of Formula II and compensates for the decomposition of the reactants of Formula III which may take place as a result of side reaction in aqueous solvents. Since the compounds of Formula III are rapidly converted in water into removable easily neutral nitrogen-containing heterocyclic compounds, the purity of the penicillins is hardly impaired by such an excess. In general therefore it will in each case be the less valuable reactant which is used in excess.

Processing of the reaction batches in order to isolate the penicillins and their salts, is carried out in the manner which is generally customary in penicillin chemistry, for example by removing the solvent and reprecipitating or recrystallizing. The salts can be precipitated particularly simply from ethereal solutions. Thus, the new penicillins can be precipitated as socium salts from an ethereal solution, with the aid of sodium 2-ethylhexanoate.

If the compounds of Formula II contain silyl groups, the hydrolytic elimination of the silyl radicals takes place in the course of the customary aqueous working up of the reaction batches, if appropriate at an acid pH, for example pH 1.5 to 5.

New active compounds which may be mentioned individually are: D-α-[(3-phenyl-imidazolidin-2-on-1-yl)-carbonylamino]-benzylpenicillin, D-α-[(3-phenyl-imidazolidin-2-on-1-yl)-carbonylamino]-p-hydroxy-benzylpenicillin, D-α-[(3-phenylimidazolidin-2-on-1-yl)-carbonylamino]-α-(cyclohexa-1,4-dien-1-yl)-methylpenicillin, D-α-[(3-m-chlorophenyl-imidazolidin-2-on-1-yl)-carbonylamino]-benzylpenicillin, D-α-[(3-m-chlorophenyl-imidazolidin-2-on-1-yl)-carbonylamino]-p-hydroxy-benzylpenicillin, D-α-[(3-m-chlorophenyl-imidazolidin-2-on-1-yl)-carbonylamino]-α-(cyclohexa-1,4-dien-1-yl)-methylpenicillin, D-α-[(3-m-cyanophenyl-imidazolidin-2-on-1-yl)-carbonylamino]-benzylpenicillin, D-α-[(3-m-cyanophenyl-imidazolidin-2-on-1-yl)-carbonylamino]-p-hydroxy-benzylpenicillin, D-α-[(3-m-cyanophenyl-imidazolidin-2 -on-1-yl)-carbonylamino]-α-(cyclohexa-1,4-dien-1-yl)-methylpenicillin, D-α-[(3-p-methoxyphenyl-imidazolidin-2-on-1-yl)-carbonylamino]-benzylpenicillin, D-α-[(3-p-methoxyphenyl-imidazolidin-2-on-1-yl)-carbonylamino]-p-hydroxy-benzylpenicillin, D-α-[(3-o-methoxyphenyl-imidazolidin-2-on-1-yl)-carbonylamino]-benzylpenicillin, D-α-[(3-o-methoxyphenyl-imidazolidin-2-on-1-yl)-carbonylamino]-p-hydroxy-benzylpenicillin, D-α-[(3-o-methoxyphenyl-imidazolidin-2-on-1-yl-carbonylamino]-α-(cyclohexa-1,4-dien-1-yl)-methylpenicillin, D-α-{[3-(p-methylaminosulphonyl)-phenyl-imidazolidin-2-on-1-yl]-carbonylamino}-benzylpenicillin, D-α{[3-(p-methylaminosulphonyl)-phenyl-imidazolidin-2-on-1-yl]carbonylamino}-p-hydroxy-benzylpenicillin, D-α-

{[3-(p-methylaminosulphonyl)-phenyl-imidazolidin-2-on-1-yl]-carbonylamino}-α-(cyclohexa-1,4-dien-1-yl)-methylpenicillin, D-α-[(3-p-sulphophenylimidazolidin-2-on-1-yl)-carbonylamino]-benzylpenicillin, D-α-[(3-p-sulphophenyl-imidazolidin-2-on-1-yl)-carbonylamino]-p-hydroxy-benzylpenicillin, D-α-[(3-p-sulphophenyl-imidazolidin-2-on-1-yl)-carbonylamino]-α-(cyclohexa-1,4-dien-1-yl)-methylpenicillin, D-α-[(3-p-hydroxyphenyl-imidazolidin-2-on-1-yl)-carbonylamino]-benzylpenicillin, D-α- [(3-p-hydroxyphenylimidazolidin-2-on-1yl)-carbonylamino]-p-hydroxy-benzylpenicillin, D-α-[(3-p-hydroxyphenyl-imidazolidin-2-on-1-yl-carbonylamino]-α-(cyclohexa-1,4-dien-1-yl)-methylpenicillin, D-α-[(3-p-carboxyphenyl-imidazolidin-2-on-1-yl)-carbonylamino]-benzylpenicillin, D-α-[(3-p-carboxyphenyl-imidazolidin-2-on-1-yl)-carbonylamino]-p-hydroxy-benzylpenicillin and D-α-[(3-p-carboxyphenyl-imidazolidin-2-on-1-yl)-carbonylamino]-α-(cyclohexa-1,4-dien-1-yl)-methylpenicillin.

The active compounds according to the invention couple a strong and broad antimicrobial activity with a low toxicity. These properties permit their use as chemotherapeutic agents in medicine and as compounds for preserving inorganic and organic materials, in particular organic materials normally subject to bacterial infestation or growth such as polymers, lubricants, paints, fibres, leather, paper and timber, foodstuffs and water. The compounds are active against a broad spectrum of micro-organisms, including Gram negative and Gram positive bacteria and bacteria-like micro-organisms. They are therefore particularly suitable for the prophylaxis and chemotherapy of local and systemic infections, caused by these pathogens, in human medicine and veterinary medicine. Typical of such pathogens are the following:

Micrococcaceae, such as Staphylococci, for example *Staphylococcus aureus, Staph. epidermidis, Staph. aerogenes* and *Gaffkya tetragena* (Staph. = Staphylococcus);

Lactobacteriaceae, such as Streptococci, for example *Streptococcus pyogenes*, α- or β-haemolytic Streptococci, non-(γ)-haemolytic Streptococci, *Str. viridans, Str. faecalis* (Enterococci), *Str. agalacetiae, Str. lactis, Str. equi, Str. anaerobis* and *Diplococcus pneumoniae* (Pneumococci) (Str. = Streptococcus);

Neisseriaceae, such as Neisseriae, for example *Neisseria gonorrhoeae* (Gonococci), *N. meningitidis* (Meningococci), *N. catarrhalis* and *N. flava* (N = Neisseria);

Corynebacteriaceae, such as Coryebacteria, for example *Corynebacterium diphtheriae, C. pyogenes, C. diphtherodes, C. acnes, C. parvum, C. bovis, C. renale, C. ovis* and *C. murisepticum*, Listeria bacteria, for example *Listeria monocytogenes*.

Enterobacteriaceae, such as Escherichiae bacteria of the Coli group: Escherichia bacteria, for example *Escherichia coli*, Enterobacter bacteria, for example *E. aerogenes* and *E. cloacae*, Klebsiella bacteria, for example *K. pneumoniae, K. pneumoniae* and *K. ozaenae*, Erwiniae, for example *Erwinia spec.*, Serratia, for example *Serratia marcescens* (E. = Enterobacter) (K. = Klebsiella), Proteae bacteria of the Proteus group: Proteus, for example *Proteus vulgaris, Pr. morganii, Pr. rettgeri* and *Pr. mirabilis*, Providencia, for example *Providencia sp.* (Pr. = Proteus), Salmonelleae: Salmonella bacteria, for example *Salmonella paratyphi A* and *B, S. typhi, S. enteritidis, S. cholerae suis* and *S. typhi murium* (S. = Salmonella, and Shigella bacteria, for example *Shigella dysenteriae, Sh. ambigua, Sh. flexneri, Sh. boydii* and *Sh. sonnei* (Sh. = Shigella);

Pseudomonadaceae, such as Pseudomonas bacteria, for example *Pseudomonas aeruginosa* and *Ps. pseudomallei* (Ps. = Pseudomonas), and Aeromonas bacteria, for example *Aeromonas liquefaciens* and *A. hydrophila* (A. = Aeromonas);

Spirillaceae, such as Vibrio bacteria, for example *Vibrio cholerae, V. proteus* and *V. fetus* (V. = Vibrio).

Parvobacteriaceae or Brucellaceae, such as Pasteurella bacteria, for example *Pasteurella multocida, Past. pestis* (Yersinia), *Past. pseudotuberculosis* and *Past. tolarensis* (Past. = Pasteurella);

Haemophilus bacteria, for example *Haemophilus infuenzae, H. ducreyi, H. suis, H. canis* and *H. aegypitcus* (H. = Haemophilus), Bordetella bacteria, for example *Bordetella pertussis* and *B. Bronchiseptica* (B. = Bordetella).

Bacteroidaceae, such as Bacteroides bacter, for example *Bacteroides fragilis* and *B. serpens* (B. = Bacteroides), Fusiforme bacteria, for example *Fusobacterium fusiforme*, and Sphaerophorus bacteria, for example *Sphaerophorus necrophorus, Sph. necroticus* and *Sph. pyrogenes* (Sph. = Sphaerophorus);

Bacilaceae, such as aerobic spore-forming organisms, for example *Bacillus anthracis (B. subtilis* and *B. cereus* (B. = Bacillus) and anaerobic spore-forming Clostrdia, for example *Clostridium perfringens, Cl. septicium, Cl. oedematien, Cl. histolyticum, Cl. tetani* and *Cl. botulinum* (Cl. = Clostridium).

The compounds according to the invention can thus be used in the treatment of infectious conditions of the respiratory passages and of the pharyngeal cavity; otitis; pharyngitis; pneumonia; peritonitis; pyelonephritis, cystitis; endocarditis; systemic infections; bronchitis; arthritis; and various other local infections.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the requied diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a power mixture, granulating or slugging, adding a lubriant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat or shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

This invention further provides a method of combating (including prevention, relief and cure of) infections in human and non-human animals, which comprises administering thereto an antibacterially effective amount of a compound of the invention, alone or in admixture with a diluent or in the form of a pharmaceutical composition according to the invention.

The β-lactam or a salt can be administered perorally, parenterally (for examfple intramuscularly, intraperitoneally or intravenously), rectally or locally, but preferably orally or parenterally. Preferred pharmaceutical compositions and medicaments are therefore those adapted for oral and parenteral administration.

The invention also includes, for use in veterinary medicine, medicated fodder comprising a compound according to the invention and a consumable carrier which can also be nutritious. Examples of suitable nutritious materials are oil cake, grains, such as barley, fish meal, soya bean meal, exhausted sugar beet chips, silage, hay and skimmed mil.

In general a suitable antibacterial effect both in human medicine and in verterinary medicine is observed upon administration of these compounds in total daily doses of from about 5 to about 1,000, preferably 10 to 200 mg/kg of body weight. Optionally, this can be in the form of several individual administrations, in order to achieve more consistent blood levels. An individual administration contains the active compound in amounts of from about 1 to about 250, especially of 13 to 60, mg/kg of body weight. However, it can be necessary to deviate from these guidelines and in particular to do so as a function of the nature and body weight of the subject to be treated, the nature and the severity of the illness, the nature of the preparation and of the administration of the medicine, and the time or interval over which the administration takes place. Thus in some cases less than 5 mg/kg of active compound will give a suitable response while in other cases more than 1,000 mg/kg of active compound may be indicated. The particular optimum dosage should be in each case tritrated to the particular individual and the type of administration determined by sound professional judgment.

When used as additives to feedstuffs, the new compounds, in the usual concentrations and preparations, can be administered together with the feedstuff or the feedstuff preparations, or in the drinking water. By these means, subchronic infections of Gram negative or Gram positive bacteria can be reduced, thereby promoting growth and improving feedstuff utilization.

In order to broaden the spectrum of action and enhance antibacterial activity, especially in the case of β-lactamase forming bacteria, the compounds can be combined with other antimicrobial active compounds, as for example penicillins such as oxacillin or dicloxacillin which are penicillinase-resistant. Similarly, the compounds of the invention can also be combined with aminoglycoside antibiotics, such as for example gentamicin, sisomicin, kanamicin, amikacin or tobramicin.

The activity of the compounds can be demonstrated by way of example, by the following in vitro model.

The compounds of Examples 1, 5 and 11 were diluted to a content of 100 $\mu$g/ml with Müller-Hinton nutrient broth, with the addition of 0.1% by weight of glucose. In each case, the nutrient solution contained 1 $\times 10^5$ to $2 \times 10^5$ bacteria per milliliter. Tubes containing this culture were in each case incubated for 24 hours and the degree of turbidity was then determined, freedom from turbidity indicating antibacterial action. At a dosage of 100 $\mu$g/ml, the following bacterial cultures were free from turbidity:

*Klebsiella pneumoniae: Enterobacter aerogenes sp.; Providencia; Serratia marcescens; E. coli BE; Salmonella sp.; Shigella sp.;* Proteus, indole-negative and indole-positive; *Staphylococcus aureus* 133, *Neisseria catarrhalis sp.; Diplococcus pneumonia sp.; Streptococcus pyogenes W.; Enterococcus sp.; Lactobacillus sp.; Corynebacterium diphteriae gravis; Corynebacterium pyogenes M; Clostridium tetani* and *Pseudomonas aeruginosa sp.*

Table 1 shows the action of the compound of Example 1 against bacteria in vivo. White mice of the CF$_1$ strain were infected introperitoneally with the bacteria indicated. Two administrations of the compound, 30 and 90 minutes after infection were made. The ED$_{100}$ is the dose at which 100% of the infected animals survive after 24 hours.

Table 1

| Germ | Dose in mg of the β-lactam antibiotic per kg/body weight (subcutaneously) |
|---|---|
| Escherichia coli Neum. | 2 × 150 |

Table 1-continued

| Germ | Dose in mg of the β-lactam antibiotic per kg/body weight (subcutaneously) |
|---|---|
| Klebsiella 63 | 2 × 100 |

The α-aminobenzylpenicillin used in the following examples which follow contained about 14% of water; however, anhydrous α-aminobenzylpenicillin (see U.S. Pat. No. 3,144,445) can be used equally well.

The α-amino-p-hydroxybenzylpenicillin used in the examples contained about 13% of water; however, anhydrous α-amino-p-hydroxybenzylpenicillin can be used equally well.

The 6-[2-amino-2-(1,4-cyclohexadien-1-yl)-acetamido]-penicillanic acid used in the examples was substantially anhydrous.

The water content of the starting compounds is of little or no importance for carrying out the process according to the invention.

"Ampicillin" refers to α-aminobenzylpenicillin having the D (R) configuration at the carbon atom designated *. "Amoxicillin" refers to α-amino-4-hydroxybenzylpenicillin which similarly has the D configuration and "epicillin" refers to α-amino-α-(1,4-cyclohexadien-1-yl)methylpenicillin, also with the D configuration.

The process according to the invention and particular embodiments of the compounds of the invention will be further illustrated by the following examples. Unless otherwise stated, the NMR spectra of the compounds according to the invention were recorded in CD$_3$OD solution. The codes in brackets denote:

s = singlet
d = doublet
t = triplet
q = quartet and
m = multiplet

Unless otherwise stated, the IR spectra of the compounds according to the invention are recorded in NUJOL (TM) paraffin oil suspensions.

Explanation of the abbreviations used in the examples:

| vol. | = volume |
|---|---|
| pts. by wt. | = parts by weight |
| pts. by vol. | = parts by volume |
| hrs. | = hours |
| hr. | = hour |
| THF | = tetrahydrofuran |
| ether | = diethyl ether |
| ethyl acetate | = acetic acid ethyl ester |
| room temperature | = about 20° C |
| abs. | = absolute |
| decomp. p. | = decomposition point |

The yields quoted in % denote yields in % of theory. All the temperatures quoted are in ° C.

EXAMPLE 1

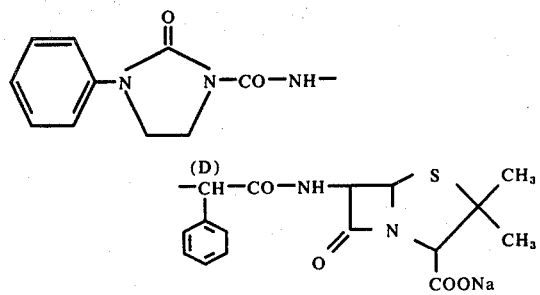
A)

Triethylamine was added to a suspension of 8.0 pts. by wt. of ampicillin trihydrate in 80 pts. by vol. of 80% aqueous tetrahydrofurane, while stirring, until the pH of the mixture had reached 8.0. 4.4 pts. by wt. of 1-chlorocarbonyl-2-oxo-3-phenyl-imidazolidine were then introduced, while cooling with ice/water, and, during this addition, the pH was kept at 7.0–7.5 by an approprite addition of triethylamine. The mixture was further stirred until no further triethylamine had to be added in order to maintain this pH (about ½ hour). The mixture was diluted with about 100 pts. by vol. of water, the tetrahydrofurane was substantially removed by means of a rotary evaporator and the residual aqueous solution was acidified, after it had been covered with a layer of ethyl acetate, to pH 2, while cooling and stirring. The organic phase was separated off, washed with water and dried over MgSO$_4$. After removing the drying agent, sodium D-α-[(3-phenyl-imidazolidin-2-on-1-yl)-carbonylamino]-benzylpenicillin was precipitated in a crystalline form by adding an approximately 1 molar ethereal solution (containing about 10% of methanol) of sodium 2-ethylcaproate.

Yield: 10.2 pts. by wt.

β-Lactam content: 95%.

IR bands (carbonyl region) at: 1,780, 1,755, 1,705, 1,690, 1,600, 1,545 and 1,520 cm$^{-1}$.

NMR signals (CD$_3$OD) at τ= 2.25–2.9 (m, 10H), 4.4 (s, 1H9, 4.45–4.65 (AB, 2H), 5.85 (s, 1H), 6.05–6.2 (s, 4H), 8.4 (s, 3H) and 8.5 ppm (s, 3H).

The substance contained 1.5 mols of water of crystallisation. This is taken into account in the calculated analytical data:

Calculated C, 53.3; H, 5.0; N, 11.9; S, 5.5 . k
Found: C 53.5; H, 5.5; N, 11.9; S, 5.6.

The electropherogram displayed only one spot having an antibiotic action against B. subtilis, E. coli and Pseudomonas aeruginosa.

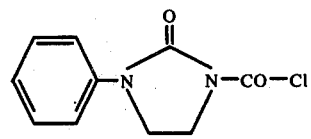
B)

This substance was obtained as a crystalline precipitate from 1-phenyl-2-oxo-imidazoline and 1.1 to 1.3 molar equivalents of phosgene in tetrahydrofurane at 20° C in about 20 hours.

Melting point: 208° C.

Calculated:C, 53.5, H, 4.0Cl 15.8, N, 12.5, Found: C, 53.4, H, 4.3, Cl, 16.1, N, 11.8.

EXAMPLE 2

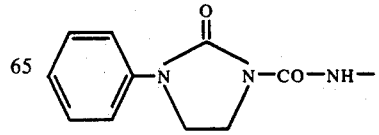

-continued

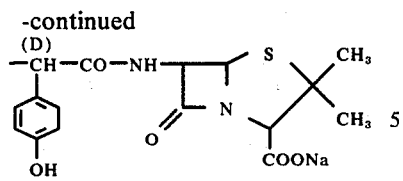

This penicillin was obtained in the manner described in Example 1 from 2.5 pts. by wt. of amoxicillin trihydrate and 1.35 pts. by wt. of 1-chlorocarbonyl-2-oxo-3-phenyl-imidazolidine. After the acidification, some of the free penicillic acid (1.9 pts. by wt.) did not dissolve in the ethyl acetate and crystallised out. 0.9 pt. by wt. of the sodium salt of the penicillin could be precipitated from the organic phase. The free penicillic acid is converted into the sodium salt by dissolving it in dimethylacetamide (1- pts. by vol.), adding 1 molar sodium 2-ethylhexanoate solution (3.2 pts. by vol.) and pouring the mixture into ether (150 pts. by vol.). A total of 2.8 pts. by wt. of sodium D-α-[(3-phenyl-imidazolidin-2-on-1-yl)-carbonylamino]-p-hydroxybenzylpenicillin were obtained in a crystalline form.

β-Lactam content: 82%.

IR bands(carbonyl region) at: 1,775, 1,755, 1,700, 1,650, 1,600, 1,580 and 1,530 cm⁻¹.

NMR signals (CD₃OD) at τ = 2.3–3.3 (m, 9H), 4.4–4.6 (3H), 5.8 (s, 1H), 5.9–6.2 (s, 4H) and 8.3–8.6 ppm (d, 6H).

The NMR spectrum showed that the substance still contained 0.5 molar equivalent of dimethylacetamide, 0.23 molar equivalent of sodium 2-ethylhexanoate and 2.5 molar equivalents of water. This is taken into account in the following calculated analytical data:

Calculated:C, 51.1, H, 5.6, N, 11.0, S, 4.6, Found: C 51.1, H, 5.4, N,10.8, S, 4.4.

The electropherogram showed one spot having antibiotic action against *B. subtilis*, *E. coli* and *Pseudomonas aeruginosa*.

EXAMPLE 3

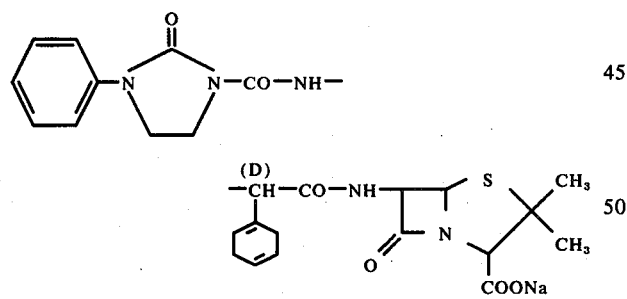

This penicillin was obtained in the manner described in Example 1 from 2.5 pts. by wt. of epicillin and 1.6 pts. by wt. of 1-chlorocarbonyl-2-oxo-3-phenyl-imidazolidine.

Yield: 3.4 pts. by wt. of sodium D-α-[(3-phenyl-imidazlidin-2-on-1-yl)-carbonylamino]-α-(1,4-cyclohexadienyl-1)-methylpenicillin.

β-Lactam content: 85%.

IR bands(carbonyl region) at: 1,780, 1,765, 1,710 (shoulder), 1,690, 1,640, 1,590 and 1,535 cm⁻¹.

NMR signals (CD₃OD) at τ = 2.2–2.9 (m, 5H), 4.1 (s, 1H), 4.3 (s, 2H), 4.5 (s. 2H), 5.0 (s, 1H), 5.8 (s, 1H), 6.0–6.3 (s,4H), 7.1–7.5 (broad s, 4H) and 8.3–8.6 ppm (d, 6H).

It could be seen from the NMR spectrum that the substance contained about 1.3 molar equivalents of water, 0.2 molar equivalent of ethyl acetate and 0.05 molar equivalent of sodium 2-ethylhexanoate. This is taken into account in the following calculated analytical data:

Calculated: C, 53.5; H, 5.6; N, 11.4 ; S, 5.2. Found:C 53.6; H, 6.4; N, 11.4; S, 5.3.

EXAMPLE 4

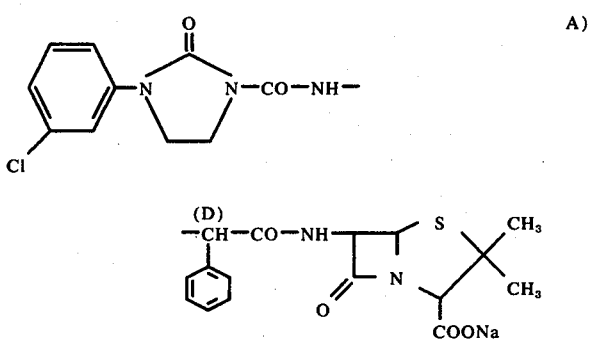

This penicillin was obtained in the manner described in Example 1 from 4.0 pts. by wt. of ampicillin trihydrate and 2.6 pts. by wt. of 1-chlorocarbonyl-2-oxo-3-(m-chloro)-phenylimidazolidine.

Yield: 6.0 pts. by wt. of sodium D-α-[(3-m-chlorophenylimidazolidin-2-on-1yl)-carbonylamino]-benzyl-penicillin.

β-Lactam content: 78%.

IR bands(carbonyl region) at: 1,775, 1,745, 1,695, 1,635, 1,580, 1,530 and 1,505 cm⁻¹. NMR signals (CD₃OD) at τ= 2.1–2.9 (m, 9H), 4.3 (s, 1H), 4.3–4.6 (AB, 2H), 5.8 (s, 1H) 5.9–6.2 (s, 4H) and 8.2–8.6 ppm (d, 6H).

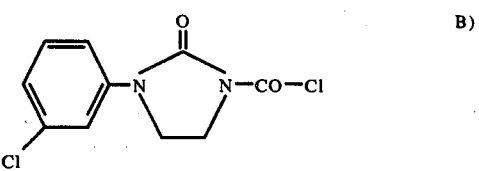

A solution of 4.6 pts. by vol. of phosgene in 15 pts. by vol. of tetrahydrofurane was added dropwise, at 8–10° C, to a solution of 9.8 pts. by wt. of 1-(m-chloro)-phenyl-2-oxoimidazolidine in 100 pts. by vol. of tetrahydrofurane and the mixture was then stirred for about a further 4 hours at 20° C. The precipitate which had deposited was filtered off, washed with ether and dried in a desiccator over NaOH.

Yield: 3.7 pts. by wt. of 1-chlorocarbonyl-2-oxo-3-(m-chloro)-phenyl-imidazolidine.

Melting point: 136° C.

A further 4.8 pts. by wt. of substances having the same melting point could be obtained from the mother liquors.

Calculated: C, 46.3; H, 3.1; Cl, 27.4, N, 10.8. Found: C, 45.9, H, 3.1, Cl, 27.4, N, 10.8.

EXAMPLE 5

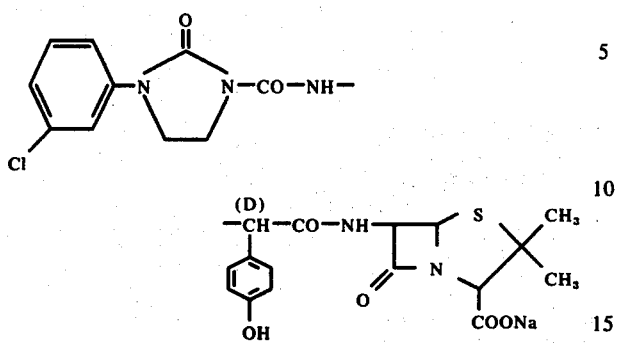

This penicillin could be prepared in the manner explained in Example 1 from 1.5 pts. by wt. of amoxicillin trihydrate and 0.9 pt. by wt. of 1-chlorocarbonyl-2-oxo-3-(m-chloro)-phenyl-imidazolidine.

Yield: 2. 3 pts. by wt. of sodium D-α-[(3-m-chlorophenyl- imidazolidin-2-on-1-yl-carbonylamino]-p-hydroxybenzylpenicillin.

β-Lactam content: 92%.

NMR signals (CD$_3$OD) at τ = 2.2–3.3 (m, 8H), 4.3–4.7 (m, 3H), 5.8 (s, 1H), 5.9–6.3 (s, broad, 4H) and 8.2–8.6 ppm (d, 6H).

IR bands (carbonyl region) at: 1,775, (1,750), 1,700, 1,680 (shoulder), 1,640, 1,580, 1,535 and 1,500 cm$^{-1}$.

It could be seen from the NMR spectrum that the substance contained about 2 molar equivalents of water and 0.1 molar equivalent of sodium 2-ethylhexanoate. This is taken into account in the calculated analytical data:

Calculated: C, 48.6, H, 4.7, N, 10.6, S, 4.8, Cl, 5.4,
Found: C, 48.5; H, 4.7, N, 10.5 , S, 4.8; Cl, 6.1.

EXAMPLE 6

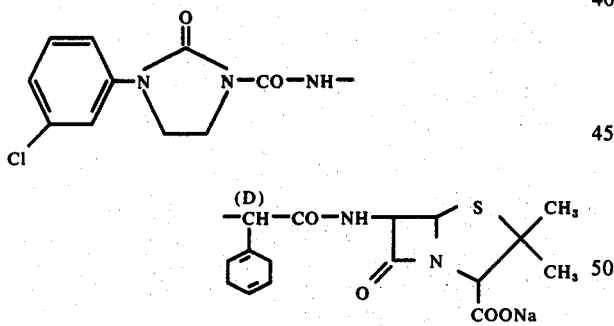

This penicillin was obtained in the manner described in Example 1 from 1.0 pt. by wt. of epicillin and 0.74 pt. by wt. of 1-chlorocarbonyl-2-oxo-3-(m-chloro)-phenyl-imidazolidine.

Yield: 1.8 pts. by wt. of crystalline sodium D-α-[(3-m-chlorophenyl-imidazolidin-2-on-1-yl)-carbonylamino]-α-(1,4-cyclohexadienyl-1)-methyl-penicillin.

β-Lactam content: 81%.

NMR signals (CD$_3$OD) at τ = 2.1–2.8 (m, 4H), 4.0 (s, 1H), 4.2 (s, 2H), 4.4 (s, 2H), 4.9 (s, 1H), 5.7 (s, 1H), 6.0 (s, 4H), 7.2 (s, broad, 4H) and 8.2–8.45 ppm (d. 6H).

IR bands (carbonyl region) at: 1,775, (1,775), 1,700, 1,695 (shoulder), 1,640, 1,685, 1,550 and 1,500 cm$^{-1}$.

EXAMPLE 7

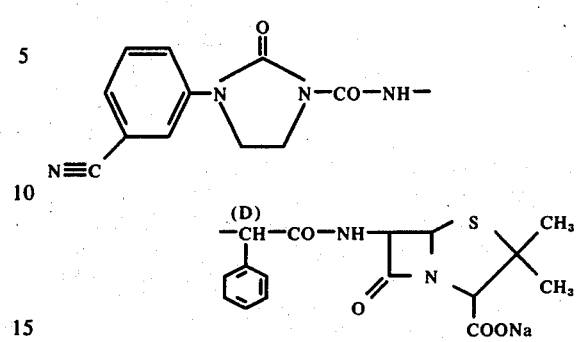

This penicillin was obtained in the manner described in Example 1 from 4.0 pts. by wt. of ampicillin trihydrate and 2.4 pts. by wt. of 1-chlorocarbonyl-2-oxo-3-(m-cyano)-phenylimidazolidine.

Yield: 5.0 pts. by wt. of sodium D-α-[(3-m-cyanophenyl-imidazolidin-2-on-1-yl-carbonylamino]-benzylpenicillin. β-Lactam content: 87%.

IR bands (carbonyl region) at: 1,780, 1,765 (shoulder), 1,720, 1,695 (shoulder), 1,650, 1,590, 1,540 and 1,520 cm$^{-1}$.

NMR signals (CD$_3$OD) at τ = 1.9–2.7 (m, 9H), 4.4 (s, 1H), 4.4–4.65 (AB, 2H), 5.8 (s, 1H), 5.9–6.2 (s, broad, 4H), and 8.3–8.6 ppm (d, 6H).

It could be seen from the NMR spectrum that the substance contained 1.5 molar equivalents of water, 0.2 molar equivalent of ethyl acetate and 0.11 molar equivalent of sodium 2-ethylhexanoate. This is taken into account in the calculated analytical data:

Calculated: C, 53.4; H, 5.0; N, 13.0; S, 5.0.
Found: C, 53.5; H, 5.7; N, 13.3; S, 5.7.

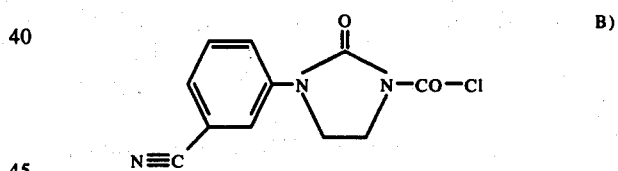

B)

A solution of 4.6 pts. by vol. of phosgene in 15 pts. by vol. of tetrahydrofurane was added dropwise, at 10° C, to a suspension of 9.4 pts. by wt. of 1-(m-cyano)-phenyl-2-oxo-imidazolidine in 100 pts. by vol. of tetrahydrofurane, while stirring, and the mixture was then stirred for a further 20 hours at 20° C. The product was filtered off and recrystallised from ethyl acetate.

Yield: 7.5 pts. by wt. of 1-chlorocarbonyl-2-oxo-3-(m-cyano)-phenyl-imidazolidine.

Melting point: 170° C.

Calculated: C, 52.9; H, 3.2; Cl, 14.2; N, 16.8.
Found: C, 52.7; H, 3.4; Cl, 14.2; N, 16.7.

EXAMPLE 8

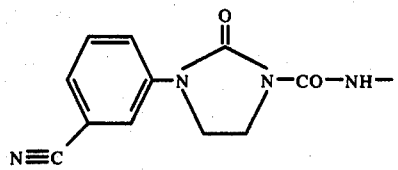

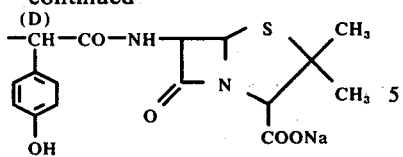

This penicillin was prepared in the manner described in Example 1 from 1.5 pts. by wt. of amoxicillin trihydrate and 0.89 pt. by wt. of 1-chlorocarbonyl-2-oxo-3-(m-cyano)-phenyl-imidazolidine.

Yield: 2.5 pts. by wt. of sodium D-α-[(3-m-cyanophenyl-imidazolidine-2-on-1-yl)-carbonylamino]-p-hydroxybenzylpenicillin.

β-Lactam content: 92%.

IR bands (carbonyl region) at: 1,775 (shoulder), 1,765, 1,717, 1,660, 1,600, 1,540 (shoulder), 1,525 (shoulder) and 1,505 cm$^{-1}$.

NMR signals (CD$_3$OD) at τ = 1.9–3.3 (m, 8H), 4.3–4.7 (m, 3H), 5.8 (s, 1H), 5.9–6.2 (s, broad, 4H) and 8.2–8.6 ppm (d, 6H).

According to the NMR spectrum, the substance contained 2 molar equivalents of water. This is taken into account in the calculated analytical data:

Calculated: C, 50.9; H, 4.6; N, 13.2; S, 5.0.
Found: C, 50.4; H, 4.7; N, 13.1; S, 5.5.

EXAMPLE 9

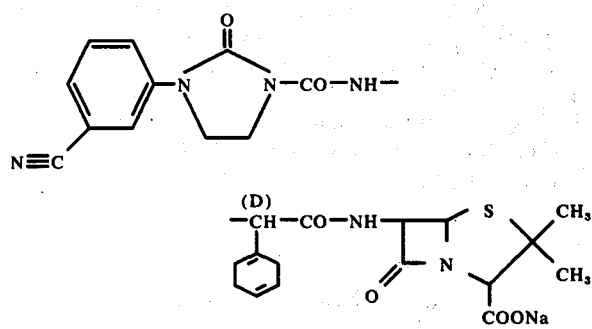

This penicillin was obtained from the reaction, as described in Example 1, of 1.0 pt. by wt. of epicillin with 0.71 pt. by wt. of 1-chlorocarbonyl-2-oxo-3-(m-cyano)-phenylimidazolidine.

Yield: 1.7 pts. by wt. of crystalline sodium D-α-[(3-m-cyanophenyl-imidazolidin-2-on-1-yl)-carbonylamino]-α-(1,4-cyclohexadienyl-1)-methylpenicillin.

β-Lactam content: 81%.

IR signals (carbonyl region) at: 1,775, 1,755 (shoulder), 1,700 1,690 (shoulder), 1,635, 1,580, 1,540 and 1,500 cm$^{-1}$.

NMR signals (CD$_3$OD) at τ = 1.8–2.6 (m, 4H), 4.0 (s, 1H), 4.2 (s, 2H), 4.4 (s, 2H), 4.9 (s, 1H), 5.75 (s, 1H), 5.8–6.15 (s, broad, 4H), 7,05–7.45 (s, broad, 4H) and 8.2–8.6 ppm (d, 6H).

EXAMPLE 10

A)

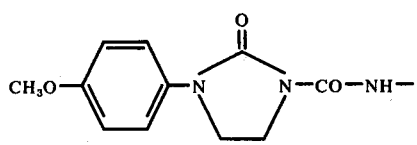

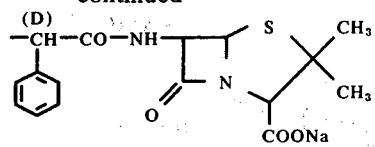

This penicillin was obtained in a crystalline form in the manner described in Example 1 from 4.0 pts. by wt. of ampicillin trihydrate and 2.5 pts, by wt. of 1-chlorocarbonyl-2-oxo-3-(p-methoxy)-phenyl-imidazolidine.

Yield: 6.3 pts. by wt. of sodium D-α-[(3-p-methoxy-phenylimidazolidin-2-on-1-yl)-carbonylamino]-benzyl-penicillin.

β-Lactam content: 84%.

IR bands (carbonyl region) at: 1,775, 1,755, 1,685, 1,635, 1,585, 1,525 (broad) and 1,500 cm$^{-1}$.

NMR signals (CD$_3$OD) at τ = 2.4–2.8 (7H), 2.95–3.2 (d, 2H), 4.4–4.6 (m, 3H), 5.85 (s, 1H), 6.1 (s, 4H), 6.25 (s, 3H), 8.4 (s, 3H) and 8.5 ppm (s, 3H).

The substance contained 1.6 molar equivalents of water. This is taken into account in the calculated analytical data:

Calculated: C, 52.4; H, 5.1; N, 11.3; S, 5.2.
Found: C, 52.0; H, 5.1; N, 11.3; S, 5.6.

B)

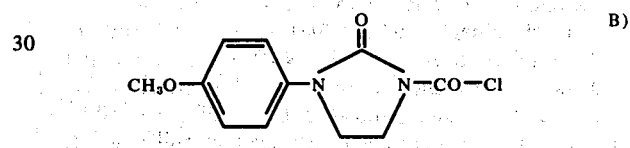

33 pts. by wt. of 1-(p-methoxy)-phenyl-2-oxo-imidazolidine were added to a mixture of 23 pts. by wt. of phosgene and 500 pts. by vol. of tetrahydrofurane and a mixture of 20 pts. by wt. of triethylamine and 100 pts. by vol. of tetrahydrofurane is then added dropwise at −5° C. The mixture was then left to stand for 20 hrs. at 20° C. Some of the acid chloride sought precipitated together with triethylamine hydrochloride and some of it dissolved. It was isolated from the precipitate by boilng the latter thoroughyl with tetrahydrofurane and evaporating the extracts. The filtrate from the precipitate present in the reaction mixture was evaporated. A crude product remained, which was purified together with the crude product obtained from the tetrahydrofurane extracts by recrystallising twice from toluene.

Yield: 28 pts. by wt. of 1-chlorocarbonyl-2-oxo-3-(p-methoxy)-phenyl-imidazolidine.

Melting point: 182°–83° C.

Calculated: C, 51.9; H, 4.3; N, 11.0; Cl, 14.0.
Found: C, 51.7; H, 4.6; N, 11.0; Cl, 14.2.

C)

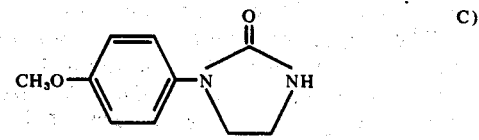

31.3 pts. by wt. of N-(p-methoxyphenyl)-1-amino-ethane-2-carboxylic acid hydrazide were dissolved in a warm 1:1 mixture (1,500 pts. by vol.) of ethanol and dichloromethane, 5.5 pts. by wt. of hydrogen chloride (dissolved in ethanol) were added and 17.5 pts. by wt. of isoamyl nitrite were then added dropwise at 0° C.

The mixture was left to stand at 4° C for 18 hrs. and was then distilled under normal pressure until a temperature of 78° C was reached in the vapour. The mixture was then boiled under reflux for 20 hrs., all the volatile matter was stripped off and the residue was treated with nitromethane. The crystalline precipitate which forms was filtered off and recrystallised from ethanol.

Yield: 7.8 pts. by wt. of 1-(p-methoxy)-phenyl-2-oxo-imidazolidine.

Melting point: 210°–212° C.

Calculated: C, 62.5; H, 6.3; N, 14.6; O, 16.7.
Found: C, 62.8; H, 6.2; N, 15.2; O, 16.7.

EXAMPLE 11

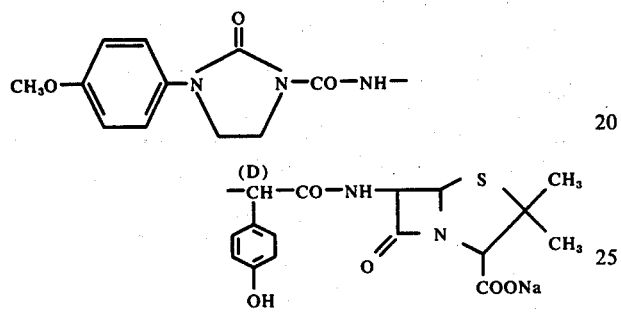

This penicillin was obtained in the manner described in Example 1 from 1.5 pts. by wt. of amoxicillin trihydrate and 0.91 pt. by wt. of 1-chlorocarbonyl-2-oxo-3-(p-methoxy)-phenyl-imidazolidine.

Yield: 2.1 pts. by wt. of sodium D-$\alpha$-[(3-p-methoxyphenyl)-imidazolidin-2-on-1-yl)-carbonylamino]-p-hydroxybenzylpenicillin.

$\beta$-Lactam content: 93%.

IR bands (carbonyl region) at: 1,770 (shoulder), 1,750, 1,700, 1,650, 1,580–1,600, 1,540 (shoulder and 1,500 cm$^{-1}$. NMR signals (CD$_3$OD) at = 2.5–3.35 (m, 8H), 4.4–4.7 (m, 3H), 5.85 (s, 1H), 6.2 (s, 4H), 6.25 (s, 3H), 8.4 (s, 3H) and 8.5 ppm (s, 3H).

It could be seen from the NMR spectrum that the substance contained about 1.9 molar equivalents of water, 0.02 molar equivalent of ethyl acetate and 0.035 molar equivalent of sodium 2-ethylhexanoate. This is taken into account in the calculated analytical data:

Calculated:C, 50.7; H, 5.1; N, 10.8; S, 5.0. Found:C, C, 50.4; H, 6.2; N, 10.8; S, 5.2.

EXAMPLE 12

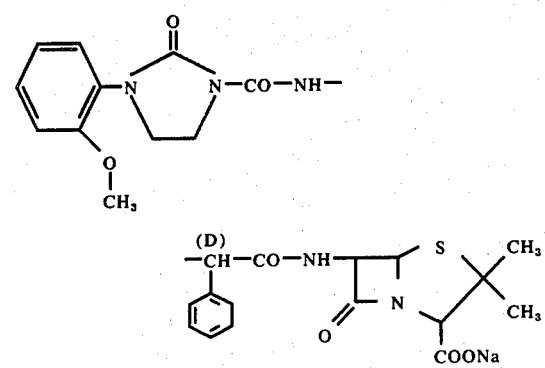

The penicillin was obtained when 4.0 pts. by wt. of ampicillin trihydrate were reacted, in the manner described in Example 1, with 2.5 pts. by wt. of 1-chlorocarbonyl-2-oxo-3-(o-methoxy)-phenyl-imidazolidine.

Yield: 5.4 pts. by wt. of sodium D-$\alpha$-[(3-o-methoxyphenylimidazolidin-2-on-1-yl)-carbonylamino]-benzylpenicillin.

$\beta$-Lactam content: 79%.

IR bands (carbonyl region) at: 1,755, 1,710, 1,650, 1,590, 1,530 (shoulder), 1,515 (shoulder) and 1,490 cm$^{-1}$.

NMR signals (CD$_3$OD) at $\tau$ = 2.4–3.2 (m, 9H), 4.4 (s, 1H), 4.45–4.65 (AB, 2H), 5.85 (s, 1H), 6.15 (broad, s, 7H), 8.45 (s, 3H) and 8.5 ppm (s, 3H).

According to NMR, the substance contained about 0.125 molar equivalent of sodium 2-ethylhexanoate and about 1.45 molar equivalents of water. This is taken into account in the calculated anlaytical data:

Calculated:C, 52.8; H, 5.2; N, 11.0; S, 5.0. Found:C, 52.9; H, 5.4; N, 10.7; S, 5.0.

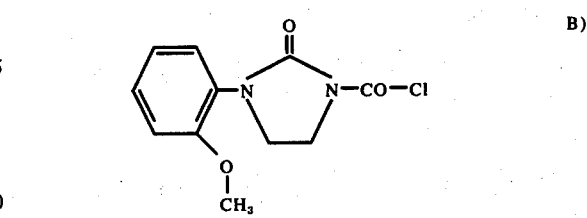

B)

This substance was obtained in the manner described in Example 14 B from 15.0 pts. by wt. of 1-(o-methoxy)-phenyl-2-oxo-imidazolidine, 8.0 pts. by vol. of phosgene, 9.0 pts. by wt. of triethylamine and about 300 pts. by vol. of tetrahydrofurane.

Yield: 12.0 pts. by wt. of 1-chlorocarbonyl-2-oxo-3-(o-methoxy)-phenyl-imidazolidine.

Melting point: 88°–91° C.

Calculated:C, 51.9; H, 4.3; N, 11.0; Cl, 14.0. Found:C, 51.9; H, 4.2; N, 11.0; Cl, 14.3.

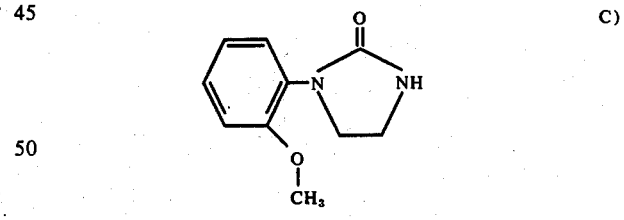

C)

This substance was obtained in the manner described in Example 14 C from 34.0 pts. by wt. of N-(o-methoxyphenyl)-1-aminoethane-3-carboxylic acid hydrazide, 6.0 pts. by wt. of hydrogen chloride and 19.0 pts. by wt. of isoamyl nitrite in ethanol/dichloromethane.

Yield: 5.5 pts. by wt. of 1-(o-methoxy)-phenyl-2-oxo-imidazolidine.

Melting point: 143°–46° C.

The substance contained 0.33 molar equivalent of water. This is taken into account in the claculated analytical data:

Calculated:C, 60.8; H, 6.4; N, 14.2. Found:C, 60.6; H, 6.3; N, 14.4.

EXAMPLE 13

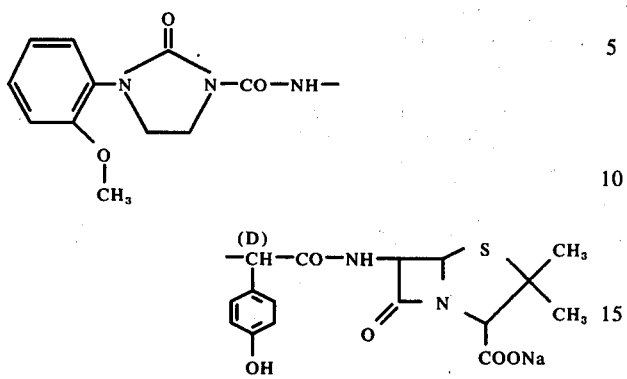

This penicillin was obtained when 1.5 pts. by wt. of amoxicillin trihydrate were reacted, in the manner described in Example 1, with 0.91 pt. by wt. of 1-chlorocarbonyl-2-oxo-3-(o-methoxy)-phenyl-imidazolidine.

Yield: 2.2 pts. by wt. of sodium D-α-[(3-o-methoxy-phenylimidazolidin-2-on-1-yl)-carbonylamino]-p-hydroxybenzylpenicillin.

β-Lactam content: 91%

IR bands (carbonyl region) at: 1,755, 1,705, 1,650, 1,595, 1,530 (shoulder), 1,515 (shoulder) and 1,495 cm$^{-1}$.

NMR signals (CD$_3$OD) at τ = 2.5–3.4 (m, 8H), 4.35–4.65 (s, broad, 3H), 5.8 (s, 1H), 6.15 (s, broad, 7H), 8.4 (s, 3H) and 8.5 ppm (s, 3H).

EXAMPLE 14

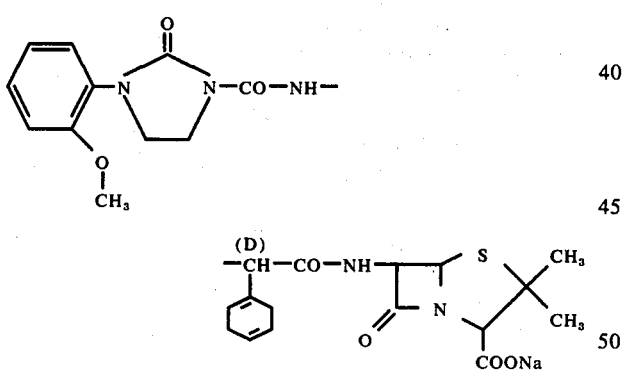

This penicillin was obtained in the manner described in Example 1 from 1.0 pt. by wt. of epicillin and 0.73 pt. by wt. of 1-chlorocarbonyl-2-oxo-3-(o-methoxy)-phenyl-imidazolone.

Yield: 1.6 pts. by wt. of sodium D-α-[(3-o-methoxy-phenylimidazolidin-2-on-1-yl)-carbonylamino]-α-(1,4-cyclohexadienyl-1)-methylpenicillin.

β-Lactam content: 80%.

IR bands (carbonyl region) at: 1,755, 1,705, 1,650, 1,590, 1,530 (shoulder), 1,250 (shoulder) and 1,485 cm$^{-1}$.

NMR signals (CD$_3$OD) at τ = 4.5–3.1 (m, 4H), 4.1 (s, 1H), 4.3 (s, 2H), 4.5 (s, 2H), 5.0 (s, 1H), 5.8 (s, 1H), 6.15 (s, broad, 7H), 7.3 (s, 4H), 8.35 (s, 3H) and 8.45 ppm (s, 3H).

EXAMPLE 15

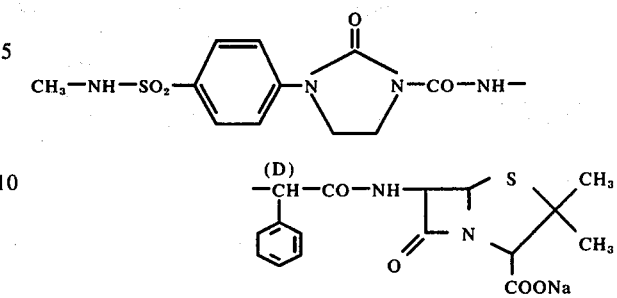

This penicillin was obtained in the manner described in Example 1 from 2.5 pts. by wt. of ampicillin trihydrate and 2.0 pts. by wt. of 1-chlorocarbonyl-2-oxo-3-(p-methylamino-sulphonyl)-phenyl-imidazolidine.

Yield: 3.5 pts. by wt. of sodium D-α-[(3-p-methylaminosulphonylphenyl-imidazolidin-2-on-1-yl)-carbonylamino]-benzylpenicillin.

β-Lactam content: 93%.

IR bands (carbonyl region) at: 1,755, 1,705, 1,650, 1,585, 1,535 (shoulder) and 1,520 cm$^{-1}$.

NMR signals (CD$_3$OD) at τ = 1.9–2.8 (m, 9H), 4.3 (s, 1H), 4.35–4.6 (AB, 2H), 5.8 (s, 1H), 6.1 (s, broad, 4H), 7.4 (s, 3H), 8.4 (s, 3H) and 8.5 ppm (s, 3H).

It could be seen from the NMR spectrum that the substance contains about 1 molar equivalent of water and 0.06 molar equivalent of sodium 2-ethylhexanoate. This has been taken into account in the calculated analytical data:

Calculated:C, 48.5; H, 4.7; N, 12.3; S, 9.4. Found:C, 48.7; H, 5.1; N, 11.8; S, 9.2.

B)

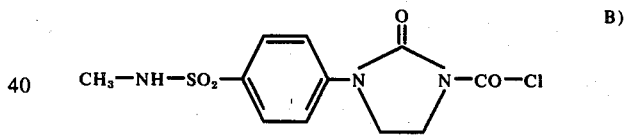

A solution of 2.5 pts. by wt. of phosgene in 10 pts. by vol. of benzonitrile was added to a suspension of 5.0 pts. by wt. of 1-(p-methylaminosulphonylphenyl-2-oxo-imidazolidine in 35 pts. by vol. of benzonitrile and the mixture was then warmed to 80° C for about 90 minutes. The mixture was then cooled and the precipitate which had deposited was filtered off, washed with ether and dried over NaOH in a desiccator.

Yield: 6.0 pts. by wt. of 1-chlorocarbonyl-2-oxo-3-(p-methylaminosulphonyl)-phenyl-imidazolidine.

Melting point: 194°–95° C.

Calculated:C, 41.6; H, 3.8; Cl, 11.2; N, 13.2; S, 10.1. Found:C, 41.5; H, 3.9; Cl, 11.0; N, 12.7; S, 10.1.

C)

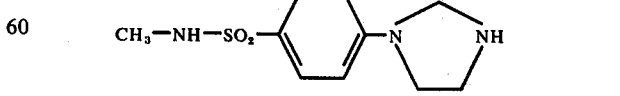

16.0 pts. by wt. of 1-phenyl-2-oxo-imidazolidine were introduced, at 12°–15° C, into 33 pts. by vol. ov chlorosulphonic acid. The mixture was then allowed to come to room temperature and was stirred until the evolution of HCl subsides. The mixture was then warmed to 40°

C for a further 10 minutes and, after cooling, was poured onto 300 pts. by wt. of ice and the yellow precipitate was filtered off, washed well with water and then introduced into a mixture of 60 pts. by vol. of 30–40% strength aqueous methylamine solution and 60 pts. by vol. of methanol, while cooling. The mixture was stirred for a further 1 hour and the precipitate was filtered off and, after drying, recrystallised from acetonitrile.

Yield: 19.3 pts. by wt. of 1-(p-methylaminosulphonyl)-phenyl-2-oxo-imidazolidine.

Melting point: 213°–14° C.

Calculated (x 0.66 mol of $H_2O$):C, 44.9; H, 5.2; N, 15.7; S, 12.0. Found:C, 44.9; H, 4.8; N, 16.0; S, 12.3.

EXAMPLE 16

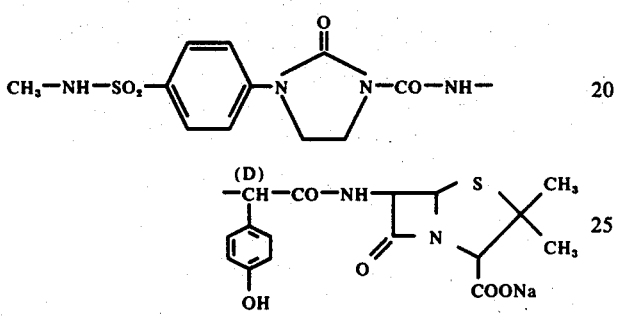

This penicillin was obtained when 1.5 pts. by wt. of amoxicillin trihydrate are reacted, in the manner described in Example 1, with 1.1 pts. by wt. of 1-chlorocarbonyl-2-oxo-3-(p-methylaminosulphonyl)-phenyl-imidazolidin.

Yield: 1.8 pts. by wt. of sodium D-α-[(3-p-methylaminosulphonylphenyl-imidazolidin-2-on-1-yl)-carbonylamino]-p-hydroxybenzylpenicillin.

β-Lactam content: 90%.

IR bands (carbonyl region) at: 1,750, 1,706, 1,650, 1,600 (shoulder), 1,580, 1,530 (shoulder) and 1,515 (shoulder) $cm^{-1}$.

NMR signals ($CD_3OD$) at $\tau = 2.2$ (s, 4H), 2.5–2.8 (d, 2H), 3.0–3.3 (d, 2H), 4.5 (s, broad, 3H), 5.8 (s, 1H), 6.1 (s, broad, 4H), 7.45 (s, 3H), 8.4 (s, 3H) and 8.5 ppm (s, 3H).

According to the NMR spectrum, the substance still contained 0.3 molar equivalent of sodium 2-ethylhexanoate and 2.5 molar equivalents of water. This has been taken into account in the calculated analytical data:

Calculated: C, 46.3; H, 5.1; N, 11.0; S, 8.4. Found: C, 46.4; H, 5.3; N, 11.1; S, 8.5.

EXAMPLE 17

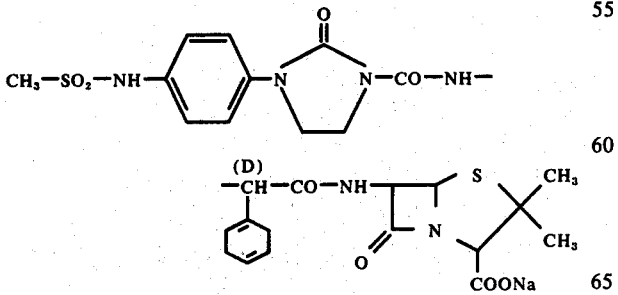

This penicillin was obtained in the manner described in Example 1 from 2.0 pts. by wt. of epicillin and 1.8 pts. by wt. of 1-chlorocarbonyl-2-oxo-3-(p-methylaminosulphonyl)-phenyl-imidazolidine.

Yield: 3.4 by wt. of sodium D-α-[(3-p-methylaminosulphonylphenyl-imidazolidin-2-on-1-yl)-carbonylamino]-α-(1,4-cyclohexadienyl-1)-methylpenicillin.

β-Lactam content: 92%

IR bands (carbonyl region) at: 1.750, 1,705, 1,650, 1,580, 1,530 (shoulder) and 1,515 (shoulder) $cm^{-1}$.

NMR signals ($CD_3OD$) at $\tau = 2.2$ (s, 4H), 4.05 (s, 1H), 4.3 (s, 2H), 4.5 (s, 2H), 5.0 (s, 1H), 5.8 (s, 1H), 6.0 (s, broad, 4H), 7.3 (s, broad, 4H), 7.45 (s, 3H), 8.35 (s, 3H) and 8.45 ppm (s, 3H).

According to the NMR spectrum, the substance contained about 0.14 molar equivalent of sodium 2-ethylhexanoate and 1.0 molar equivalent of water. This has been taken into account in the calculated analytical data:

Calculated: C, 47.8; H, 5.0; N, 11.9; S, 9.1. Found: C, 47.9; H, 5.0; N, 11.7; S, 9.1.

EXAMPLE 18

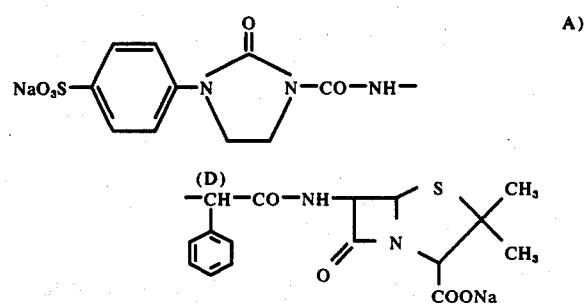

A)

This penicillin was obtained in the manner described in Example 1 from 2.0 pts. by wt. of ampicillin trihydrate and 1.5 pts by wt. of 1-chlorocarbonyl-2-oxo-3-(p-sulfonyl)-phenylimidazolidine (acidification to ph 1.0).

β-Lactam content: 84%

IR bands (carbonyl region) at: 1760, 1705, 1660, 1600 and 1540 – 1510 $cm^{-1}$.

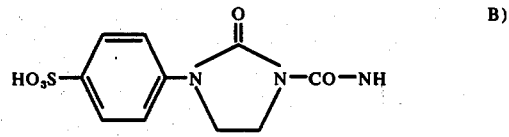

B)

This substance was obtained as a precipitate from 1-(p-sulfo)-phenyl-2-oxo-imidazolidine and phosgene in benzonitril at elevated temperature, after evaporation of the solvent and recristallisation.

IR-bands (carbonyl region) at: 1780 and 1580 $cm^{-1}$.

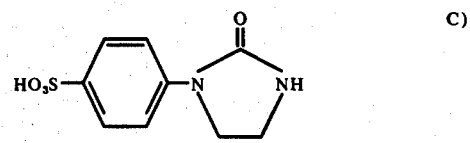

C)

This substance was obtained from 1-(p-chlorosulfonyl)-phenyl-2-oxo-imidazolidin (24.0 pts. by wt.), 1 n NaOH (110 pts. by vol.) and 150 pts. by vol. H₂at refluxtemperature.

melting point: > 250° C
IR-bands (carbonyl region) at: 1770 and 1580 cm⁻¹
NMR signals (D₂) at τ = 2.0 – 2.6 (g, 4H) and 6.1 – 6.8 ppm (m, 4H).

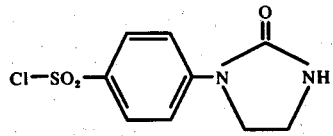

D)

This substance was obtained from 1-phenyl-2-oxo-imidazolidine and chlorosulfonic acid.

Melting point: 210° C (det.)
Calculated: C, 41.5; H, 3.5; N, 10.8; Cl, 13.6; S, 12.3. Found: C, 41.2; H, 3.4; N, 10.2; Cl, 13.1; S, 12.3.
NMR-signals (d6-DMF) at τ = 1.9 (s, 2H), 2.3 (s, 2H), 5.7 – 6.2 (m, 2H) and 6.2 – 6.7 ppm (m, 2H).

What is claimed is:

1. A compound selected from the group consisting of a penicillin of the formula:

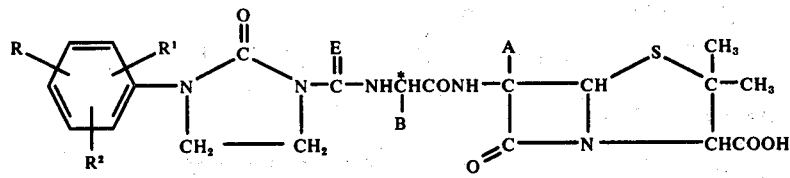

and the pharmaceutically acceptable salts thereof, wherein
the carbon atom designated * constitutes a center of chirality;
A is hydrogen or methoxy;
B is phenyl, hydroxyphenyl, halophenyl, methoxyphenyl, cyanophenyl, methylsulfonylphenyl, thienyl, cyclohexenyl or cyclohexa-1,4-dien-1-yl;
each of R, R¹ and R² is independently selected from the group consisting of hydrogen, halo, lower alkyl, halo(lower)alkyl, carboxy, formyl, carbo(lower alkoxy), lower alkanoyl, cyano, carbamyl, lower alkylcarbamyl, di(lower alkyl)carbamyl, lower alkylamino, di(lower alkyl)amino, pyrrolidino, piperidino, formamido, lower alkanamido, N-(lower alkyl)formamido, N-(lower alkyl)lower alkanamido, lower alkylidenimino, lower alkylsulfonamido, n-(lower alkyl)lower alkylsulfonamido, sulfamino, N-(lower alkyl)sulfamino, amidino, di(-lower alkyl)aminomethylidenimino, pyrrolidinomethylidenimino, guanido, nitro, azido, carbo(lower alkoxy)amino, N-(lower alkyl)carbo(-lower alkoxy)-amino, hydroxy, lower alkoxy, formyloxy, lower alkanoyloxy, lower alkoxycarbonyloxy, carbamyloxy, N-(lower alkyl)carbamyloxy, N,N-di(lower alkyl)-carbamyloxy, pyrrolidinocarboxyloxy, sulfamyl, N-(lower alkyl)sulfamyloxy, N,N-di(lower alkyl)-sulfamyloxy, mercapto, lower alkylthio, trifluoromethylthio, lower alkylsulfonyl, sulfo, lower alkylsulfinyl, trifluoromethylsulfonyl, sulfamyl, N-(lower alkyl)sulfamyl, N,N-di(lower alkyl)sulfamyl, pyrrolidinosulfonyl, and sulfothio; and
E is oxygen or sulfur.

2. A compound according to claim 1 wherein said penicillin is of the formula:

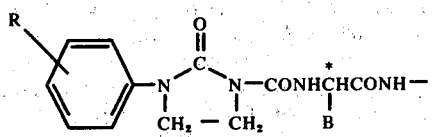

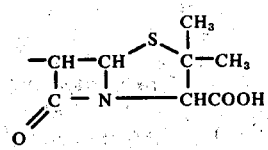

and the pharmaceutically acceptable salts thereof, wherein
the carbon atom designated * constitutes a center of chirality;
B is phenyl, hydroxyphenyl, chlorophenyl, cyclohexenyl or cyclohexa-1,4-dien-1-yl; and
R is hydrogen, halo, cyano, lower alkoxy or lower alkylsulfamyl.

3. A compound according to claim 2 wherein
B is phenyl, 4-hydroxyphenyl or cyclohexa-1,4-dien-1-yl; and
R is hydrogen, chloro, cyano, methoxy or methylsulfamyl.

4. A compound according to claim 1 which is a salt of said penicillin, said salt being selected from the group consisting of the sodium, potassium, magnesium, calcium, aluminium, di(lower alkyl)amine, tri(lower alkyl)amine, procaine, dibenzylamine, N,N'-dibenzylethylenediamine, N-benzyl-β-phenylethylamine, N-methylmorpholine, N-ethylmorpholine, 1-ephenamine, dehydroabietylamine, N,N'-bis-dehydroabietylethylenediamine and N-(lower alkyl)piperidine salts.

5. A compound according to claim 1 wherein said penicillin is α-(3-phenylimidazolidin-2-on-1-ylcarbonylamino)-benzylpenicillin.

6. A compound according to claim 1 wherein said penicillin is α-(3-phenylimidazolidin-2-on-1-ylcarbonylamino)-4-hydroxybenzylpenicillin.

7. A compound according to claim 1 wherein said penicillin is α-(3-phenylimidazolidin-2-on-1-ylcarbonylamino)-α-(cyclohexa-1,4-dien-1-yl)methylpenicillin.

8. A compound according to claim 1 wherein said penicillin is α-[3-(4-methoxyphenyl)imidazolidin-2-on-1-yl-carbonylamino]benzylpenicillin.

9. A compound according to claim 1 wherein said penicillin is α-[3-(4-methoxyphenyl)imidazolidin-2-on-1-yl-carbonylamino]-4-hydroxybenzylpenicillin.

10. A compound according to claim 1 wherein said penicillin is α-[3-(4-methylaminosulfonylphenyl)imidazolidin-2-on-1-ylcarbonylamino]benzylpenicillin.

11. A compound according to claim 1 wherein said penicillin is α-[3-(4-methylaminosulfonylphenyl- )imidazolidin-2-on-1-ylcarbonylamino]-4-hydroxybenzylpenicillin.

12. A pharmaceutical composition for treating bacterial infections in humans and other animals which comprises an antibacterially effective amount of a compound according to claim 1 in combination with a pharmaceutically acceptable nontoxic carrier.

13. A method of treating bacterial infections in humans and other animals which comprises administering thereto an antibacterially effective amount of a compound according to claim 1.

14. A growth-promoting composition which comprises an antibacterially effective amount of a compound according to claim 1 in combination with an edible carrier.

15. A method of promoting growth in livestock animals which comprises administering to such animals a growth-promoting amount of a compound according to claim 1 in combination with an edible carrier.

* * * * *

UNITED STATES PATENT OFFICE
CERTIFICATE OF CORRECTION

Patent No. 4,031,229　　　　　　　　Dated June 21, 1977

Inventor(s) Hans-Bodo König et al.

It is certified that error appears in the above-identified patent and that said Letters Patent are hereby corrected as shown below:

Column 1, line 62, after "N,N" -- di -- should be inserted.

Column 3, line 48, "dihydroabietyle-" should read -- dehydroabietyle- --.

Column 5, line 34, "prsence" should read -- presence --.

Column 7, line 9, after "3.0", "." should be -- , --.

Column 7, line 21, "tetr hydrofuran" should read -- tetrahydrofuran --.

Column 9, line 51, "Coryebacteria" should read -- Corynebacteria --.

Column 9, line 53, "diphtherodes" should read -- diphtheroides-

Column 10, line 14, "tolarensis" should read -- tularensis --.

Column 10, line 20, "bacter" should read -- bacteria --.
Column 10, line 27, "Bacilaceae" should read -- Bacillaceae --
Column 10, line 28, after "cereus" -- ) --.
Column 11, line 2, "lubriant" should read -- lubricant --.
Column 11, line 21, "or" should read -- of --.
Column 11, line 52, "examfple" should read -- example --.
Column 11, line 63, "mil" should read -- milk --.
Column 12, line 16, "tritrated" should read -- titrated --.
Column 14, line 32, "1H9" should read -- 1H) --.

Column 14, line 39, "K" should be deleted

UNITED STATES PATENT AND TRADEMARK OFFICE
CERTIFICATE OF CORRECTION

PATENT NO. : 4,031,229

DATED : June 21, 1977

INVENTOR(S) : Hans-Bodo König et al

It is certified that error appears in the above-identified patent and that said Letters Patent are hereby corrected as shown below:

Col. 15, line 21, correct spelling of "total".
Col. 15, line 60, correct spelling of "imidazolidin".
Col. 17, line 67, change "(1,775)" to -- (1,750) --.
Col. 19, line 58, change "7,05" to -- 7.05 --.
Col. 20, line 44, correct spelling of "boiling".
Col. 21, line 48, delete "C,".
Col. 23, line 21, correct spelling of "described".
Col. 23, line 63, change "1,250" to -- 1,520 --.
Col. 24, line 65, change "ov" to -- of --.
Col. 26, line 3, after "3.4" insert -- pts. --.
Col. 27, line 1, change "$H_2$" to -- $H_2O$ --.

Col. 27, line 5, change "$(D_2)$" to -- $(D_2O)$ --.

Signed and Sealed this

Eighteenth Day of July 1978

[SEAL]

Attest:

RUTH C. MASON
*Attesting Officer*

DONALD W. BANNER
*Commissioner of Patents and Trademarks*